US010398774B2

(12) United States Patent
Robert et al.

(10) Patent No.: US 10,398,774 B2
(45) Date of Patent: Sep. 3, 2019

(54) HUMAN MONOCLONAL ANTIBODIES AGAINST AXL

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); INSTITUT REGIONAL DU CANCER DE MONTPELLIER, Montpellier (FR)

(72) Inventors: Bruno Robert, Montpellier (FR); Christel Larbouret, Montpellier (FR); Pierre Martineau, Montpellier (FR); Marie-Alix Poul, Montpellier (FR)

(73) Assignees: INSERM (INSTITUT NATIONAL DE LA SANTÉ ET DE LA RECHERCHE MÉDICALE), Paris (FR); UNIVERSITE DE MONTPELLIER, Montpellier (FR); INSTITUT REGIONAL DU CANCER DE MONTPELLIER, Montpellier (FR)

( * ) Notice: Subject to any disclaimer, the term of this patent is extended or adjusted under 35 U.S.C. 154(b) by 66 days.

(21) Appl. No.: 15/534,178

(22) PCT Filed: Dec. 8, 2015

(86) PCT No.: PCT/EP2015/079003
§ 371 (c)(1),
(2) Date: Jun. 8, 2017

(87) PCT Pub. No.: WO2016/091891
PCT Pub. Date: Jun. 16, 2016

(65) Prior Publication Data
US 2017/0340734 A1    Nov. 30, 2017

(30) Foreign Application Priority Data

Dec. 9, 2014   (EP) .................................... 14306982

(51) Int. Cl.
*C07K 16/28*     (2006.01)
*A61K 39/395*    (2006.01)
*A61K 39/00*     (2006.01)

(52) U.S. Cl.
CPC ........ *A61K 39/39558* (2013.01); *C07K 16/28* (2013.01); *C07K 16/2863* (2013.01); *A61K 39/00* (2013.01); *A61K 2039/505* (2013.01)

(58) Field of Classification Search
CPC ............ C07K 16/00–468; C07K 16/28; C07K 16/2863; C07K 16/30; A61K 39/395–39558
See application file for complete search history.

(56) References Cited

U.S. PATENT DOCUMENTS

| | | | | |
|---|---|---|---|---|
| 8,841,424 | B2 * | 9/2014 | Wirtz | C07K 16/2863 424/141.1 |
| 8,853,369 | B2 * | 10/2014 | Pei | A61K 39/39558 530/388.85 |
| 9,173,962 | B2 * | 11/2015 | Beau-Larvor | C07K 14/71 |
| 9,249,228 | B2 * | 2/2016 | Robert | C07K 16/2863 |
| 9,340,615 | B2 * | 5/2016 | Maeda | C07K 16/2863 |
| 9,409,988 | B2 * | 8/2016 | Robert | C07K 16/28 |
| 9,624,308 | B2 * | 4/2017 | Beau-Larvor | C07K 16/2863 |
| 9,689,862 | B2 * | 6/2017 | Beau-Larvor | C07K 14/71 |
| 9,975,953 | B2 * | 5/2018 | Micklem | C07K 16/2863 |
| 9,975,954 | B2 * | 5/2018 | Micklem | C07K 16/2863 |

FOREIGN PATENT DOCUMENTS

| | | |
|---|---|---|
| EP | 2 228 392 A1 | 9/2010 |
| WO | 2011/159980 A1 | 12/2011 |
| WO | 2012/175692 A1 | 12/2012 |

OTHER PUBLICATIONS

Almagro & Fransson, Frontiers in Bioscience, 13:1619-33 (Year: 2008).*
PJ Carter, Nat Rev Immunol, 6:343-357 (Year: 2006).*

* cited by examiner

*Primary Examiner* — Jessica H Roark
(74) *Attorney, Agent, or Firm* — W&C IP

(57) ABSTRACT

The present disclosure provides human monoclonal antibodies and antibody-drug conjugates against AXL and their use for the treatment of cancer.

14 Claims, 4 Drawing Sheets
Specification includes a Sequence Listing.

SEQUENCE LISTING

```
<160> NUMBER OF SEQ ID NOS: 2

<210> SEQ ID NO 1
<211> LENGTH: 119
<212> TYPE: PRT
<213> ORGANISM: Artificial
<220> FEATURE:
<223> OTHER INFORMATION: Synthetic VH region of the D4 antibody

<400> SEQUENCE: 1

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Arg Lys Asp Ser Gly Thr Ile Tyr His Trp Gly Arg Gly
            100                 105                 110

Thr Leu Val Thr Val Ser Ser
        115

<210> SEQ ID NO 2
<211> LENGTH: 111
<212> TYPE: PRT
<213> ORGANISM: Artificial
<220> FEATURE:
<223> OTHER INFORMATION: Synthetic VL region of the D4 antibody

<400> SEQUENCE: 2

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30
```

```
Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                      70                  75                  80

Gln Ala Glu Asp Glu Ala Asp Tyr Tyr Cys Lys Lys Asp Asp Tyr Ser
                85                  90                  95

Leu Arg Phe Thr Phe Gly Gly Gly Thr Lys Leu Ala Val Leu Gly
            100                 105                 110
```

HUMAN MONOCLONAL ANTIBODIES AGAINST AXL

FIELD OF THE INVENTION

The present invention relates to human monoclonal antibodies against AXL and use thereof for the treatment of cancer.

BACKGROUND OF THE INVENTION

AXL belongs to the TAM subfamily of receptor tyrosine kinases (RTKs) that also includes Tyro3 and Mer. The TAM receptors are characterized by a combination of two immunoglobin-like domains and dual fibronectin type III repeats in the extracellular region and a cytoplasmic kinase domain. The ligands for TAM receptors are Gas6 (growth-arrest-specific 6) and protein S, two vitamin-K dependent proteins that show 43% amino acid sequence identity and share similar domain structures. Each protein has an N-terminal GIa domain containing 11 g-carboxyglutamic acid residues, followed by four epidermal growth factor (EGF)-like modules, and a C-terminal sex hormone-binding globlin (SHBG)-like structure consisting of two tandem laminin G domains. The SHBG domain is both necessary and sufficient for TAM receptor binding and activation, whereas the GIa domain binds the negatively charged membrane phospholipids and plays an important role in TAM-mediated phagocytosis of apoptotic cells. TAM activation and signalling has been implicated in multiple cellular responses including cell survival, proliferation, migration and adhesion.

Dysregulation of AXL or its ligand Gas6 is implicated in the pathogenesis of a variety of human cancers. Overexpression of AXL has been reported in a wide array of human cancers (lung, prostate, breast, gastric, pancreatic, ovarian, thyroid, blood cancers, renal cell carcinoma as well as glioblastoma . . . ) and is associated with invasiveness, metastasis and negative prognosis. These findings suggest that AXL may be involved in the regulation of multiple aspects of tumorigenesis including tumor growth, invasion and angiogenesis and thus represents a target for therapeutic intervention in cancer especially for the development of anti-metastatic cancer therapy and for other multiple cancer treatment including treatment of drug resistance. Recently, AXL has been described as a major player in tumor resistance to Erlotinib in patients. Indeed, overexpression of AXL is detected in tumors from patients resistant to Erlotinib and, in vitro, sensitivity can be restored by knocking down AXL receptor in Erlotinib-resistant tumor cell lines established from patient (Zhang Z et al. Nat Genetics, 2012). The observation that AXL plays a key role in tumors having developed a resistance to TKI has also been observed in other cancer pathologies as CML resistant to Nilotinib or Imatinib (Gioa R et al Blood 2011; Dufies M et al. Oncotarget 2011) and GIST becoming resistant to Imatinib (Mahodevan D et al Oncogene 2007). Interestingly, a recent manuscript described also that AXL receptor expression correlates with anti-EGFR Cetuximab resistance (Brand T M et al. Cancer Res 2014). Furthermore, it is now well described that AXL receptor and EGFR heterodimerize at the tumor cell surface membrane (Meyer A S et al, Sci Signal 2013; Heideman M R et al., BCR 2013) and that phosphorylation of the intracellular domain of AXL can substitute for that of EGFR when tumor cells are treated with tyrosine kinase inhibitors against EGFR or HER2.

Accordingly, anti-AXL monoclonal antibodies have been described for use in the treatment of cancers. For example publications relating to anti-AXL antibodies include WO2009/063965, WO2009/062690, and WO2011/014457.

SUMMARY OF THE INVENTION

The present invention provides human monoclonal antibodies and antibody-drug conjugates against AXL and their use for the treatment of cancer. In particular, the present invention is defined by the claims.

DETAILED DESCRIPTION OF THE INVENTION

The present invention provides human monoclonal antibodies and antibody-drug conjugates against AXL. In particular, the antibodies of the present invention are characterized by one or more functional properties such that they are fully human antibodies, bind with high affinity to human AXL, are able to cross react between the murine and human form of AXL, induce internalization and degradation of the receptor, are able to favor the homodimerization of the receptor, inhibit AXL phosphorylation, inhibit cell proliferation in vitro, restore the sensibility to Nilotinib of resistant AXL-overexpressing CML cells and Imatinib-resistant GIST cells, and decrease tumor growth in vivo. In particular, the present invention provides antibodies that derive from the D4 antibody as described in the EXAMPLE.

The term "AXL" has its general meaning in the art and refers to the human AXL. AXL is also known as "Ark", "Tyro-7", "UFO", or "JTK11".

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L- CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

As used herein the term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

According to the invention, the VH region of the D4 antibody consists of the sequence of SEQ ID NO:1 which is defined as follows and the kabat numbered sequence is defined in Table A.

TABLE A kabat numbered sequence of the VH domain of D4
SEQ ID NO: 1
EVQLVESGGSLVKPGGSLRLSCAASGFTFSNYSMNWVRQAPGKGLEWI
SSISGSSRYIYYADFVKGRFTISRDNATNSLYLQMNSLRAEDTAVYYCV
RGRKDSGTIYHWGRGTLVTVSS

| Position in SEQ ID NO: 1 | Kabat numbering | Amino acid |
|---|---|---|
| 1 | H1 | E |
| 2 | H2 | V |
| 3 | H3 | Q |
| 4 | H4 | L |
| 5 | H5 | V |
| 6 | H6 | E |
| 7 | H7 | S |
| 8 | H8 | G |
| 9 | H9 | G |
| 10 | H10 | S |
| 11 | H11 | L |
| 12 | H12 | V |
| 13 | H13 | K |
| 14 | H14 | P |
| 15 | H15 | G |
| 16 | H16 | G |
| 17 | H17 | S |
| 18 | H18 | L |
| 19 | H19 | R |
| 20 | H20 | L |
| 21 | H21 | S |
| 22 | H22 | C |
| 23 | H23 | A |
| 24 | H24 | A |
| 25 | H25 | S |
| 26 | H26 | G |
| 27 | H27 | F |
| 28 | H28 | T |
| 29 | H29 | F |
| 30 | H30 | S |
| 31 | H31 | N |
| 32 | H32 | Y |
| 33 | H33 | S |
| 34 | H34 | M |
| 35 | H35 | N |
| 36 | H36 | W |

TABLE A-continued kabat numbered sequence of the VH domain of D4
SEQ ID NO: 1
EVQLVESGGSLVKPGGSLRLSCAASGFTFSNYSMNWVRQAPGKGLEWI
SSISGSSRYIYYADFVKGRFTISRDNATNSLYLQMNSLRAEDTAVYYCV
RGRKDSGTIYHWGRGTLVTVSS

| Position in SEQ ID NO: 1 | Kabat numbering | Amino acid |
|---|---|---|
| 37 | H37 | V |
| 38 | H38 | R |
| 39 | H39 | Q |
| 40 | H40 | A |
| 41 | H41 | P |
| 42 | H42 | G |
| 43 | H43 | K |
| 44 | H44 | G |
| 45 | H45 | L |
| 46 | H46 | E |
| 47 | H47 | W |
| 48 | H48 | I |
| 49 | H49 | S |
| 50 | H50 | S |
| 51 | H51 | I |
| 52 | H52 | S |
| 53 | H52A | G |
| 54 | H53 | S |
| 55 | H54 | S |
| 56 | H55 | R |
| 57 | H56 | Y |
| 58 | H57 | I |
| 59 | H58 | Y |
| 60 | H59 | Y |
| 61 | H60 | A |
| 62 | H61 | D |
| 63 | H62 | F |
| 64 | H63 | V |
| 65 | H64 | K |
| 66 | H65 | G |
| 67 | H66 | R |
| 68 | H67 | F |
| 69 | H68 | T |
| 70 | H69 | I |
| 71 | H70 | S |
| 72 | H71 | R |
| 73 | H72 | D |
| 74 | H73 | N |
| 75 | H74 | A |
| 76 | H75 | T |
| 77 | H76 | N |
| 78 | H77 | S |
| 79 | H78 | L |
| 80 | H79 | Y |
| 81 | H80 | L |
| 82 | H81 | Q |
| 83 | H82 | M |
| 84 | H82A | N |
| 85 | H82B | S |
| 86 | H82C | L |
| 87 | H83 | R |
| 88 | H84 | A |
| 89 | H85 | E |
| 90 | H86 | D |
| 91 | H87 | T |
| 92 | H88 | A |
| 93 | H89 | V |
| 94 | H90 | Y |
| 95 | H91 | Y |
| 96 | H92 | C |
| 97 | H93 | V |
| 98 | H94 | R |
| 99 | H95 | G |
| 100 | H96 | R |
| 101 | H97 | K |
| 102 | H98 | D |
| 103 | H99 | S |
| 104 | H100 | G |
| 105 | H100A | T |
| 106 | H100B | I |
| 107 | H101 | Y |

TABLE A-continued kabat numbered sequence of the VH domain of D4
SEQ ID NO: 1
EVQLVESGGSLVKPGGSLRLSCAASGFTFSNYSMNWVRQAPGKGLEWI
SSISGSSRYIYYADFVKGRFTISRDNATNSLYLQMNSLRAEDTAVYYCV
RGRKDSGTIYHWGRGTLVTVSS

| Position in SEQ ID NO: 1 | Kabat numbering | Amino acid |
|---|---|---|
| 108 | H102 | H |
| 109 | H103 | W |
| 110 | H104 | G |
| 111 | H105 | R |
| 112 | H106 | G |
| 113 | H107 | T |
| 114 | H108 | L |
| 115 | H109 | V |
| 116 | H110 | T |
| 117 | H111 | V |
| 118 | H112 | S |
| 119 | H113 | S |

Accordingly, the H-CDR1 of D4 is defined by the sequence ranging from the amino acid residue at position 31 to the amino acid residue at position 35 in SEQ ID NO:1.

Accordingly, the H-CDR2 of D4 is defined by the sequence ranging from the amino acid residue at position 50 to the amino acid residue at position 66 in SEQ ID NO:1.

Accordingly, the H-CDR3 of D4 is defined by the sequence ranging from the amino acid residue at position 99 to the amino acid residue at position 108 in SEQ ID NO:1.

According to the invention, the VL region of the D4 antibody consists of the sequence of SEQ ID NO:2 which is defined as follows and the kabat numbered sequence is defined in Table B.

TABLE B kabat numbered sequence of the VL domain of D4
SEQ ID NO: 2:
QSVLTQPASVSGSPGQSITISCAGTSSDVGGYNYVSWYQQHPGKAPKLM
IYEDSKRPSGVSNRFSGSKSGNTASLTISGLQAEDEADYYCKKDDYSLR
FTFGGGTKLAVLG

| Position in SEQ ID NO: 2 | Kabat numbering | Amino acid |
|---|---|---|
| 1 | L1 | Q |
| 2 | L2 | S |
| 3 | L3 | V |
| 4 | L4 | L |
| 5 | L5 | T |
| 6 | L6 | Q |
| 7 | L7 | P |
| 8 | L8 | A |

TABLE B-continued kabat numbered sequence of the VL domain of D4
SEQ ID NO: 2:
QSVLTQPASVSGSPGQSITISCAGTSSDVGGYNYVSWYQQHPGKAPKLM
IYEDSKRPSGVSNRFSGSKSGNTASLTISGLQAEDEADYYCKKDDYSLR
FTFGGGTKLAVLG

| Position in SEQ ID NO: 2 | Kabat numbering | Amino acid |
|---|---|---|
| 9 | L9 | S |
| - | L10 | - |
| 10 | L11 | V |
| 11 | L12 | S |
| 12 | L13 | G |
| 13 | L14 | S |
| 14 | L15 | P |
| 15 | L16 | G |
| 16 | L17 | Q |
| 17 | L18 | S |
| 18 | L19 | I |
| 19 | L20 | T |
| 20 | L21 | I |
| 21 | L22 | S |
| 22 | L23 | C |
| 23 | L24 | A |
| 24 | L25 | G |
| 25 | L26 | T |
| 26 | L27 | S |
| 27 | L27A | S |
| 28 | L27B | D |
| 29 | L27C | V |
| 30 | L28 | G |
| 31 | L29 | G |
| 32 | L30 | Y |
| 33 | L31 | N |
| 34 | L32 | Y |
| 35 | L33 | V |
| 36 | L34 | S |
| 37 | L35 | W |
| 38 | L36 | Y |
| 39 | L37 | Q |
| 40 | L38 | Q |
| 41 | L39 | H |
| 42 | L40 | P |
| 43 | L41 | G |

TABLE B-continued kabat numbered sequence of the VL domain of D4
SEQ ID NO: 2:
QSVLTQPASVSGSPGQSITISCAGTSSDVGGYNYVSWYQQHPGKAPKLM
IYEDSKRPSGVSNRFSGSKSGNTASLTISGLQAEDEADYYCKKDDYSLR
FTFGGGTKLAVLG

| Position in SEQ ID NO: 2 | Kabat numbering | Amino acid |
|---|---|---|
| 44 | L42 | K |
| 45 | L43 | A |
| 46 | L44 | P |
| 47 | L45 | K |
| 48 | L46 | L |
| 49 | L47 | M |
| 50 | L48 | I |
| 51 | L49 | Y |
| 52 | L50 | E |
| 53 | L51 | D |
| 54 | L52 | S |
| 55 | L53 | K |
| 56 | L54 | R |
| 57 | L55 | P |
| 58 | L56 | S |
| 59 | L57 | G |
| 60 | L58 | V |
| 61 | L59 | S |
| 62 | L60 | N |
| 63 | L61 | R |
| 64 | L62 | F |
| 65 | L63 | S |
| 66 | L64 | G |
| 67 | L65 | S |
| 68 | L66 | K |
| 69 | L67 | S |
| 70 | L68 | G |
| 71 | L69 | N |
| 72 | L70 | T |
| 73 | L71 | A |
| 74 | L72 | S |
| 75 | L73 | L |
| 76 | L74 | T |
| 77 | L75 | I |
| 78 | L76 | S |
| 79 | L77 | G |
| 80 | L78 | L |
| 81 | L79 | Q |
| 82 | L80 | A |
| 83 | L81 | E |
| 84 | L82 | D |
| 85 | L83 | E |
| 86 | L84 | A |
| 87 | L85 | D |
| 88 | L86 | Y |
| 89 | L87 | Y |
| 90 | L88 | C |
| 91 | L89 | K |
| 92 | L90 | K |
| 93 | L91 | D |
| 94 | L92 | D |
| 95 | L93 | Y |
| 96 | L94 | S |
| 97 | L95 | L |
| 98 | L95A | R |
| 99 | L96 | F |
| 100 | L97 | T |
| 101 | L98 | F |
| 102 | L99 | G |
| 103 | L10 | G |
| 104 | L101 | G |
| 105 | L102 | T |
| 106 | L103 | K |
| 107 | L104 | L |
| 108 | L105 | A |
| 109 | L10 | V |
| 110 | L106A | L |
| 111 | L107 | G |

Accordingly, the L-CDR1 of D4 is defined by the sequence ranging from the amino acid residue at position 23 to the amino acid residue at position 36 in SEQ ID NO:2.

Accordingly, the L-CDR2 of D4 is defined by the sequence ranging from the amino acid residue at position 52 to the amino acid residue at position 58 in SEQ ID NO:2.

Accordingly, the L-CDR3 of D4 is defined by the sequence ranging from the amino acid residue at position 91 to the amino acid residue at position 100 in SEQ ID NO:2.

The present invention thus provides antibodies comprising functional variants of the VL region, VH region, or one or more CDRs of D4. A functional variant of a VL, VH, or CDR used in the context of a human monoclonal antibody of the invention still allows the antibody to retain at least a substantial proportion (at least about 50%, 60%, 70%, 80%, 90%, 95% or more) of the affinity/avidity and/or the specificity/selectivity of the parent antibody (i.e. D4 antibody) and in some cases such a human monoclonal antibody or ADC of the invention may be associated with greater affinity, selectivity and/or specificity than the parent Ab. Such functional variants typically retain significant sequence identity to the parent Ab. The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parent antibody sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M
Cycloalkenyl-associated residues F, H, W, and Y
Hydrophobic residues A, C, F, G, H, I, L, M, R, T, V, W, and Y
Negatively charged residues D and E
Polar residues C, D, E, H, K, N, Q, R, S, and T
Positively charged residues H, K, and R
Small residues A, C, D, G, N, P, S, T, and V
Very small residues A, G, and S
Residues involved in turn A, C, D, E, G, H, K, N, Q, R, S, P, and formation T
Flexible residues Q, T, K, S, G, P, D, E, and R More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of D4. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide. According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence.

In some embodiments, the human monoclonal antibody of the present invention is an antibody comprising a heavy chain comprising i) a H-CDR1 having at least 90% of identity with the H-CDR1 of D4, ii) a H-CDR2 having at least 90% of identity with the H-CDR2 of D4 and iii) a H-CDR3 having at least 90% of identity with the H-CDR3 of D4.

In some embodiments, the human monoclonal antibody of the present invention is an antibody comprising a light chain comprising i) a L-CDR1 having at least 90% of identity with the L-CDR1 of D4, ii) a L-CDR2 having at least 90% of identity with the L-CDR2 of D4 and iii) a L-CDR3 having at least 90% of identity with the L-CDR3 of D4.

In some embodiments, the human monoclonal antibody of the present invention is an antibody comprising a heavy chain comprising i) a H-CDR1 having at least 90% of identity with the H-CDR1 of D4, ii) a H-CDR2 having at least 90% of identity with the H-CDR2 of D4 and iii) a H-CDR3 having at least 90% of identity with the H-CDR3 of D4 and a light chain comprising i) a L-CDR1 having at least 90% of identity with the L-CDR1 of D4, ii) a L-CDR2 having at least 90% of identity with the L-CDR2 of D4 and iii) a L-CDR3 having at least 90% of identity with the L-CDR3 of D4.

In some embodiments, the human monoclonal antibody of the present invention is an antibody comprising a heavy chain comprising i) the H-CDR1 of D4, ii) the H-CDR2 of D4 and iii) the H-CDR3 of D4.

In some embodiments, the human monoclonal antibody of the present invention is an antibody comprising a light chain comprising i) the L-CDR1 of D4, ii) the L-CDR2 of D4 and iii) the L-CDR3 of D4.

In some embodiments, the human monoclonal antibody of the present invention is an antibody comprising a heavy chain comprising i) the H-CDR1 of D4, ii) the H-CDR2 of D4 and iii) the H-CDR3 of D4 and a light chain comprising i) the L-CDR1 of D4, ii) the L-CDR2 of D4 and iii) the L-CDR3 of D4.

In some embodiments, the human monoclonal antibody of the present invention is an antibody comprising a heavy chain having at least 70% of identity with SEQ ID NO:1

In some embodiments, the human monoclonal antibody of the present invention is an antibody comprising a light chain having at least 70 of identity with SEQ ID NO:2.

In some embodiments, the human monoclonal antibody of the present invention is an antibody comprising a heavy chain having at least 70% of identity with SEQ ID NO:1 and a light chain having at least 70% of identity with SEQ ID NO:2.

In some embodiments, the human monoclonal antibody of the present invention is an antibody comprising a heavy chain which is identical to SEQ ID NO:1

In some embodiments, the human monoclonal antibody of the present invention is an antibody comprising a light chain identical to SEQ ID NO:2.

In some embodiments, the human monoclonal antibody of the present invention is an antibody comprising a heavy chain identical to SEQ ID NO:1 and a light chain identical to SEQ ID NO:2.

The antibody of the invention can be characterized by one or more of the functional or structural features of the aspects described above, or by any combination of selected functional and structural features.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a human monoclonal antibody or ADC of the invention of the present invention may be switched by known methods. Typical, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In some embodiments, the antibody of the invention is a full-length antibody. In some embodiments, the full-length antibody is an IgG1 antibody. In some embodiments, the full-length antibody is an IgG4 antibody. In some embodiments, the AXL-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antbodies are disclosed in WO2008145142, which is hereby incorporated by reference in its entirety. In some embodiments, the human monoclonal antibody or ADC of the invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In addition or alternative to modifications made within the framework or CDR regions, antibodies of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present invention may be chemically modified (e.g., one or more chemical moieties can be attached to the antibody) or be modified to alter its glycosylation, again to alter one or more functional properties of the antibody. For example, it will be appreciated that the affinity of antibodies provided by the present invention may be altered using any suitable method known in the art. The present invention therefore also relates to variants of the antibody molecules of the present invention, which have an improved affinity for AXL. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In some embodiments, the hinge region of CHI is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In some embodiments, the human monoclonal antibody of the present invention is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al. In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al, 2001 J. Biol. Chen. 276:6591-6604, WO2010106180).

In some embodiments, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (see the webpage www.urekatherapeutics.com/about/overview). Alternatively, the antibodies of the present invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the antibodies of the present invention. See for example, EP O 154 316 by Nishimura et al. and EP 0 401 384 by Ishikawa et al.

Another modification of the antibodies that is contemplated by the invention is a conjugate or a protein fusion of at least the antigen-binding region of the human monoclonal antibody of the present invention to serum protein, such as human serum albumin or a fragment thereof to increase half-life of the resulting molecule. Such approach is for example described in Ballance et al. EP0322094.

In some embodiments, the antibody is an antigen-binding fragment. Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies. The following describe exemplary formats for AXL-specific antigen-binding fragments of the invention:

F(ab')2 fragments, which are bivalent fragments comprising two Fab fragments linked by a disulfide bridge at the hinge region. These can be generated by, e.g., treating a full-length antibody with pepsin.

Fab' or Fab fragments, which are monovalent fragments consisting of the VL, VH, CL and CH1 domains. Fab fragments can be obtained, e.g., by treating an IgG antibody with papain. Fab' fragments can be obtained, e.g., by reducing the disulfide bridges of a F(ab')2 fragment using a reducing agent such as dithiothreitol.

Fd fragments, which consist essentially of the VH and CH1 domains.

Fv fragments, which consist essentially of the VL and VH domains of a single arm of an antibody and single-chain antibodies thereof. Single-chain antibodies (also known as single chain Fv (scFv) antibodies) are constructs where the VL and VH domains of an Fv fragment are joined, using recombinant methods, by a synthetic linker that enables them to be expressed as a single protein chain in which the VL and VH regions pair to form monovalent molecules (see for instance Bird et a/., Science 242, 423-426 (1988) and Huston et al., PNAS USA 85, 5879-5883 (1988)).

Fragments which comprise or consist of the VL or VH chains as well as amino acid sequence having at least 70% of identity with SEQ ID NO:1 or SEQ ID NO:2.

In some embodiments, the invention provides a multispecific antibody comprising a first antigen binding site from a human monoclonal antibody or ADC of the invention molecule described herein above and at least one second antigen binding site. In some embodiments, the second antigen-binding site is used for recruiting a killing mechanism such as, for example, by binding an antigen on a human effector cell or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radio labeled peptides), chemotherapeutic agents and prodrugs.

In some embodiments, the second antigen-binding site binds to an antigen on a human B cell, such as, e.g., CD19, CD20, CD21, CD22, CD23, CD46, CD80, CD138 and HLA-DR.

In some embodiments, the second antigen-binding site binds a tissue-specific antigen, promoting localization of the bispecific antibody to a specific tissue.

In some embodiments, the second antigen-binding site binds to an antigen located on the same type of cell as the AXL-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), a-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, Marti, MelanA, MUM-1, MUM-2, MUM-3, HLA-B7, Ep-CAM or a cancer-associated integrin, such as α5β3 integrin. Alternatively, the second antigen-binding site binds to a different epitope of AXL. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression, such as HER receptor (EGFR, HER2, HER3 or HER4), c-MET or IGFR.

In some embodiments, the second antigen-binding site is from a second human monoclonal antibody or ADC of the invention, such as a human monoclonal antibody or ADC of the invention.

Exemplary formats for the multispecific antibody molecules of the invention include, but are not limited to (i) two antibodies cross-linked by chemical heteroconjugation, one with a specificity to AXL and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivaient bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody)(EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a human monoclonal antibody or ADC of the invention of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is a human monoclonal antibody or ADC of the invention of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

The human monoclonal antibody of the present invention of the invention may be produced by any technique known in the art, such as, without limitation, any chemical, biological, genetic or enzymatic technique, either alone or in combination. For example, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid sequence encoding an antibody of the present invention. In some embodiments, the nucleic acid sequence encodes a heavy chain and/or a light chain of an antibody of the present invention.

Typically, said nucleic acid is a DNA or RNA molecule, which may be included in any suitable vector. The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or R A sequence to a host cell, so that the host cell will express the introduced gene or sequence to produce a desired substance, typically a protein or enzyme coded by the introduced gene or sequence. A host cell that receives and expresses introduced DNA or RNA bas been "transformed>>.

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculo virus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G1 1.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

In some embodiments, the human monoclonal antibody of the present invention is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *momordica charantia* inhibitor, curcin, crotin, *sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtheria toxin; and *Pseudomonas* endotoxin.

In some embodiments, the antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3): 154-169; Howard P. W. et al., Bioorg Med Chem Lett 2009; 19: 6463-6466 and Sagnou et al., Bioorg Med Chem Lett 2000; 10(18): 2083-2086.

In some embodiments, the antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

In some embodiments, a human monoclonal antibody or ADC of the invention is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, a human monoclonal antibody or ADC of the invention is conjugated to an aptamer or a ribozyme.

In some embodiments, a human monoclonal antibody or ADC of the invention is conjugated, e.g., as a fusion protein, to a lytic peptide such as CLIP, Magainin 2, mellitin, Cecropin and P18.

In some embodiments, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules Non-limiting examples of radioisotopes include $^{3}H$, $^{14}C$, $^{15}N$, $^{35}S$, $^{90}Y$, $^{99}Tc$, $^{125}I$, $^{131}I$, $^{186}Re$, $^{213}Bi$, $^{225}Ac$ and $^{227}Th$. For therapeutic purposes, a radioisotope emitting beta- or alpha-particle radiation can be used, e.g., 131I, 90Y, 211At, 212Bi, 67Cu, 186Re, 188Re, and 212Pb.

Techniques for conjugating molecule to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target humanepidermal growth factor receptor 2-positive breast cancer. Clin. Cancer Res. 16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

In another aspect, the invention relates to the human monoclonal antibody or ADC of the invention, as defined in any aspect or embodiment herein, for use as a medicament.

The human monoclonal antibodies or ADC of the invention of the present invention can be used in the treatment or prevention of disorders involving cells expressing AXL.

"Treatment" refers to the administration of an effective amount of a therapeutically active compound of the present invention with the purpose of easing, ameliorating, arresting or eradicating (curing) symptoms or disease states.

As used herein, the term "subject" is typically a human who responds to the human monoclonal antibody or ADC of the invention. Subjects may for instance include human patients having disorders that may be corrected or ameliorated by modulating AXL function or by killing of the cell, directly or indirectly.

In some embodiments, the invention provides a method for killing an AXL-expressing cell by contacting the cell with a human monoclonal antibody or ADC of the invention. In some embodiments, the invention provides a method for killing an AXL-expressing cell by contacting the cell with a human monoclonal antibody or ADC of the invention in the presence of effector cells capable of inducing an Fc-mediated effector cell response such as a CDC, ADCC or ADCP response. In this embodiment, the antibody is typically full-length and of an isotype leading to a CDC or ADCC response, such as, e.g., an IgG1 isotype. In some embodiments, the invention provides a method for killing an AXL-expressing cell by contacting the cell with an ADC of the invention.

In some embodiments, the human monoclonal antibody or ADC of the invention is particularly suitable for the treatment of cancer. Cancer cells over-expressing AXL are indeed good targets for the human monoclonal antibodies or ADC of the invention or ADCs of the invention, since more antibodies or ADCs may be bound per cell. Thus, in one aspect, the disorder involving cells expressing AXL is cancer, i.e., a tumorigenic disorder, such as a disorder characterized by the presence of tumor cells expressing AXL including, for example, disorders where the cells are from a solid tumor or hematological tumor. In particular, the anti-human monoclonal antibody or ADC of the invention or ADC of the invention may be used as treatment of hyper-proliferative diseases associated with AXL and or Gas6 expression, overexpression or activation. There are no particular limitations on the tumor tissues, and examples include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer. More preferable cancers are glioma, gastric, lung, pancreatic breast, prostate, renal, hepatic and endometrial cancers.

In some embodiments, the human monoclonal antibodies or ADC of the invention are potential activators of the innate immune response and may be used in the treatment of human immune disorders, such as sepsis, may be used as adjuvants for immunization such as for vaccine and may be used as anti-infectious agents (against bacteria, virus, parasites).

In some embodiments, the human monoclonal antibody or ADC of the invention may protect or treat thrombotic diseases such as venous and arterial thrombosis and atherothrombosis. In some embodiments, the human monoclonal antibody or ADC of the invention may protect, prevent or treat cardiovascular diseases.

In some embodiments, the human monoclonal antibody or ADC of the invention may prevent or inhibit the entry of viruses such as Lassa and Ebola viruses and may be used to treat viral infections A "therapeutically effective amount" refers to an amount effective, at dosages and for periods of time necessary, to achieve a desired therapeutic result. A therapeutically effective amount of a human monoclonal antibody or ADC of the invention may vary according to factors such as the disease state, age, sex, and weight of the individual, and the ability of the human monoclonal antibody or ADC of the invention to elicit a desired response in the individual. A therapeutically effective amount is also one in which any toxic or detrimental effects of the antibody or antibody portion are outweighed by the therapeutically beneficial effects. The efficient dosages and dosage regimens for the human monoclonal antibody or ADC of the invention depend on the disease or condition to be treated and may be determined by the persons skilled in the art. A physician having ordinary skill in the art may readily determine and prescribe the effective amount of the pharmaceutical composition required. For example, the physician could start doses of the human monoclonal antibody or ADC of the invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the compound to inhibit cell growth or to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of a human monoclonal antibody or ADC of the invention of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an AXL-specific ADC of the invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy-safety window is optimized by lowering specific toxicity such as for example by lowering the drug-antibody ratio (DAR) and/or mixing of AXL-specific ADC with unlabeled human monoclonal antibody of the invention. In some embodiments, the efficacy of the treatment is monitored during the therapy, e.g. at predefined points in time. In some embodiments, the efficacy may be monitored by measuring the level of AXL in a sample containing tumor cells, by visualization of the disease area, or by other diagnostic methods described further herein, e.g. by performing one or more PET-CT scans, for example using a labeled human monoclonal antibody or ADC of the invention, fragment or mini-antibody derived from the human monoclonal antibody or ADC of the invention of the present invention. If desired, an effective daily dose of a pharmaceutical composition may be administered as two, three, four, five, six or more sub-doses administered separately at appropriate intervals throughout the day, optionally, in unit dosage forms. In some embodiments, the human monoclonal antibodies or ADC of the invention are administered by slow continuous infusion over a long period, such as more than 24 hours, in order to minimize any unwanted side effects. An effective dose of a human monoclonal antibody or ADC of the invention of the invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of a compound of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

The invention also provides for therapeutic applications where an antibody or ADC of the invention is used in combination with at least one further therapeutic agent relevant for the disease or disorder to be treated, as described above. Such administration may be simultaneous, separate or sequential. For simultaneous administration the agents may be administered as one composition or as separate compositions, as appropriate.

Accordingly, the present invention provides methods for treating a disorder involving cells expressing AXL as described above, which methods comprise administration of a human monoclonal antibody or ADC of the invention combined with one or more additional therapeutic agents. The present invention also provides for the use of a human monoclonal antibody or ADC of the invention for the preparation of a pharmaceutical composition to be administered with at least one chemotherapeutic agent for treating such a disorder.

The further therapeutic agent is typically relevant for the disorder to be treated. Exemplary therapeutic agents include other anti-cancer antibodies or ADCs, cytotoxic agents, chemotherapeutic agents, anti-angiogenic agents, anti-cancer immunogens, cell cycle control/apoptosis regulating agents, hormonal regulating agents, and other agents described below.

In one aspect, the further therapeutic agent is at least one second antibody or ADC which binds another target such as, e.g., CD4, CD5, CD8, CD14, CD15, CD19, CD21, CD22, CD23, CD25, CD30, CD33, CD37, CD38, CD40, CD40L, CD46, CD52, CD54, CD80, CD126, B7, MUC1, tenascin, HM 1.24, or HLA-DR. For example, the second antibody may bind to a B cell antigen, including, but not limited to CD20, CD19, CD21, CD23, CD38, CD46, CD80, CD138, HLA-DR, CD22, or to another epitope on AXL. In some embodiments, the second antibody binds vascular endothelial growth factor A (VEGF-A). In some embodiments, the human monoclonal antibody or ADC of the invention of the invention is for use in combination with a specific therapeutic antibody. Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Other examples include anti-CTLA4 antibodies (e.g. Ipilimumab), anti-PD1 antibodies, anti-PDLL antibodies, anti-TIMP3 antibodies, anti-LAG3 antibodies, anti-B7H3 antibodies, anti-B7H4 antibodies or anti-B7H6 antibodies. In some embodiments, antibodies include B cell depleting antibodies. Typical B cell depleting antibodies include but are not limited to anti-CD20 monoclonal antibodies [e.g. Rituximab (Roche), Ibritumomab tiuxetan (Bayer Schering), Tositumomab (GlaxoSmithKline), AME-133v (Applied Molecular Evolution), Ocrelizumab (Roche), Ofatumumab (HuMax-CD20, Gemnab), TRU-015 (Trubion) and IMMU-106 (Immunomedics)], an anti-CD22 antibody [e.g. Epratuzumab, Leonard et al., Clinical Cancer Research (Z004) 10: 53Z7-5334], anti-CD79a antibodies, anti-CD27 antibodies, or anti-CD19 antibodies (e.g. U.S. Pat. No. 7,109,304), anti-BAFF-R antibodies (e.g. Belimumab, GlaxoSmithKline), anti-APRIL antibodies (e.g. anti-human APRIL antibody, ProSci inc.), and anti-IL-6 antibodies [e.g. previously described by De Benedetti et al., J Immunol (2001) 166: 4334-4340 and by Suzuki et al., Europ J of Immunol (1992) 22 (8) 1989-1993, fully incorporated herein by reference].

In some embodiments, the human monoclonal antibody or ADC of the invention is used in combination with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chrommomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; amino levulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and phannaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

In some embodiments, the human monoclonal antibody or ADC of the invention is used in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3 (2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the human monoclonal antibody or ADC of the invention is used in combination with a HER inhibitor. In some embodiments, the HER inhibitor is an EGFR inhibitor. GFR inhibitors are well known in the art (Inhibitors of erbB-1 kinase; Expert Opinion on Therapeutic Patents December 2002, Vol. 12, No. 12, Pages 1903-1907, Susan E Kane. Cancer therapies targeted to the epidermal growth factor receptor and its family members. Expert Opinion on Therapeutic Patents February 2006, Vol. 16, No. 2, Pages 147-164. Peter Traxler Tyrosine kinase inhibitors in cancer treatment (Part II). Expert Opinion on Therapeutic Patents December 1998, Vol. 8, No. 12, Pages 1599-1625). Examples of such agents include antibodies and small organic molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small organic molecules that bind to EGFR include ZD1839 or Gefitinib (IRESSA™; Astra Zeneca); CP-358774 or erlotinib (TARCEVA™; Genentech/OSI); and AG1478, AG1571 (SU 5271; Sugen); EMD-7200. In some embodiments, the HER inhibitor is a small organic molecule pan-HER inhibitor such as dacomitinib (PF-00299804). In some embodiments, the HER inhibitor is selected from the group consisting of cetuximab, panitumumab, zalutumumab, nimotuzumab, erlotinib, gefitinib, lapatinib, neratinib, canertinib, vandetanib, afatinib, TAK-285 (dual HER2 and EGFR inhibitor), ARRY334543 (dual HER2 and EGFR inhibitor), Dacomitinib (pan-ErbB inhibitor), OSI-420 (Desmethyl Erlotinib) (EGFR inhibitor), AZD8931 (EGFR, HER2 and HER3 inhibitor), AEE788 (NVP-AEE788) (EGFR, HER2 and VEGFR 1/2 inhibitor), Pelitinib (EKB-569) (pan-ErbB inhibitor), CUDC-101 (EGFR, HER2 and HDAC inhibitor), XL647 (dual HER2 and EGFR inhibitor), BMS-599626 (AC480) (dual HER2 and EGFR inhibitor), PKC412 (EGFR, PKC, cyclic AMP-dependent protein kinase and S6 kinase inhibitor), BIBX1382 (EGFR inhibitor) and AP261 13 (ALK and EGFR inhibitor). The inhibitors cetuximab, panitumumab, zalutumumab, nimotuzumab are monoclonal antibodies. erlotinib, gefitinib, lapatinib, neratinib, canertinib, vandetanib and afatinib are tyrosine kinase inhibitors.

In some embodiments, the human monoclonal antibody or ADC of the invention is used in combination with a c-Met inhibitor. In some embodiments the c-Met inhibitor is an anti-c-Met antibody. In some embodiments, the anti-c-met antibody is MetMAb (onartuzumab) or a biosimilar version thereof. MetMAb is disclosed in, for example, WO2006/015371; Jin et al, Cancer Res (2008) 68:4360. Other anti-c-met antibodies suitable for use in the methods of the invention are described herein and known in the art. For example, anti-c-met antibodies disclosed in WO05/016382 (including but not limited to antibodies 13.3.2, 9.1.2, 8.70.2, 8.90.3); an anti-c-met antibodies produced by the hybridoma cell line deposited with ICLC number PD 03001 at the CBA in Genoa, or that recognizes an epitope on the extracellular domain of the (3 chain of the HGF receptor, and said epitope is the same as that recognized by the monoclonal antibody); anti-c-met antibodies disclosed in WO2007/126799 (including but not limited to 04536, 05087, 05088, 05091, 05092, 04687, 05097, 05098, 05100, 05101, 04541, 05093, 05094, 04537, 05102, 05105, 04696, 04682); anti c-met antibodies disclosed in WO2009/007427 (including but not limited to an antibody deposited at CNCM, Institut Pasteur, Paris, France, on Mar. 14, 2007 under the number 1-3731, on Mar. 14, 2007 under the number 1-3732, on Jul. 6, 2007 under the number 1-3786, on Mar. 14, 2007 under the number 1-3724; an anti-c-met antibody disclosed in 20110129481; an anti-c-met antibody disclosed in US20110104176; an anti-c-met antibody disclosed in WO2009/134776; an anti-c-met antibody disclosed in WO2010/059654; an anti-c-met antibody disclosed in WO2011020925 (including but not limited to an antibody secreted from a hybridoma deposited at the CNCM, Institut Pasteur, Paris, France, on Mar. 12, 2008 under the number 1-3949 and the hybridoma deposited on Jan. 14, 2010 under the number 1-4273). In some embodiments, the cMET inhibitor is selected from the group consisting of K-252a; SU-11274; PHA-665752 and other cMET inhibitors described in WO 2002/096361; AM7; AMG-208 and other cMet inhibitors described in WO 2009/091374; JNJ-38877605 and other cMet inhibitors described in WO 2007/075567; MK-2461 and other cMet inhibitors described in WO 2007/002254 and/or WO 2007/002258; PF-04217903 and other cMet inhibitors described in WO 2007/132308; BMS 777607; GSK 136089 (also known as XL-880 and Foretinib) and other cMET inhibitors described in WO 2005/030140; BMS 907351 (also known as XL-184); EMD 1214063; LY 2801653; ARQ 197; MK 8033; PF 2341066 and other cMET inhibitors described in WO 2006/021881; MGCD 265; E 7050; MP 470; SGX 523; cMet inhibitors described in Kirin J. J. Cui, Inhibitors targeting hepatocyte growth factor receptor and their potential therapeutic applications. Expert Opin. Ther. Patents 2007; 17: 1035-45; cMet inhibitors described in WO 2008/103277; cMet inhibitors described in WO 2008/008310; cMet inhibitors described in WO 2007/138472; cMet inhibitors described in WO 2008/008539; cMet inhibitors described in WO 2009/007390; cMet inhibitors described in WO 2009/053737; cMet inhibitors described in WO 2009/024825; cMet inhibitors described in WO 2008/071451; cMet inhibitors described in WO 2007/130468; cMet inhibitors described in WO 2008/051547; cMet inhibitors described in WO 2008/053157; cMet inhibitors described in WO 2008/017361; WO 2008/145242; WO2008/145243; WO 2008/148449; WO 2009/007074; WO 2009/006959; WO 2009/024221; WO 2009/030333; and/or WO 2009/083076; cMet inhibitors described in WO 2009/093049; cMet inhibitors described in US 2008/039457; cMet inhibitors described in WO 2007/149427; cMet inhibitors described in WO 2007/050309; cMet inhibitors described in WO 2009/056692; cMet inhibitors described in WO 2009/087305; cMet inhibitors described in US 2009/197864; cMet inhibitors described in US 2009/197862; cMet inhibitors described in US 2009/156594; cMet inhibitors described in WO 2008/124849; cMet inhibitors described in WO 2008/067119; cMet inhibitors described in WO 2007/064797; cMet inhibitors described in WO 2009/045992; cMet inhibitors described in WO 2008/088881; cMet inhibitors described in WO 2007/081978; cMet inhibitors described in WO 2008/079294; cMet inhibitors described in WO 2008/079291; cMet inhibitors described in WO 2008/086014; cMet inhibitors described in WO 2009/033084; cMet inhibitors described in WO 2007/059202; cMet inhibitors described in US 2009/170896; cMet inhibitors described in WO 2009/077874 and/or WO 2007/023768; cMet inhibitors described in WO 2008/049855; cMet inhibitors described in WO 2009/026717; and cMet inhibitors described in WO 2008/046216.

In some embodiments, the human monoclonal antibody or ADC of the invention is used in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CD4+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In some embodiments, the human monoclonal antibody or ADC of the invention is used in combination with radiotherapy. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

For administration, the anti-Axl monoclonal antibody or antibody-drug conjugate is formulated as a pharmaceutical composition. A pharmaceutical composition comprising an anti-Axl monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In some embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the present invention.

FIGURES

Figure 5:
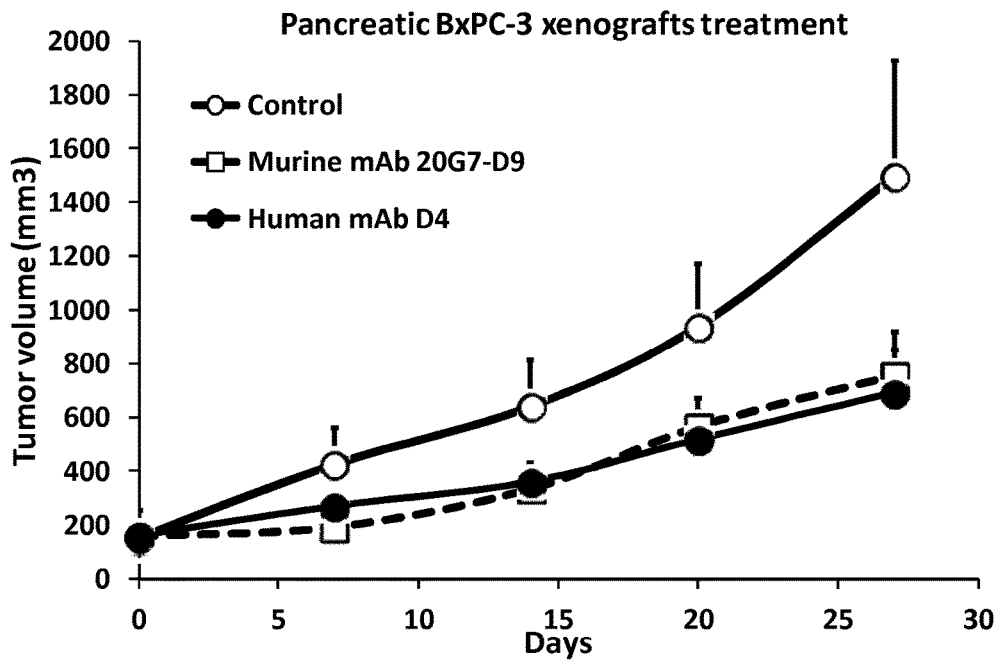

FIG. 5: Xenograft models to investigate the effects of anti-Axl antibodies on human pancreatic cancer in nude mice. BXPC3 (pancreatic cancer cells) were implanted into the right flank of athymic nude mice. Animals received 300 μg/injection of the mouse anti-human monoclonal antibody (D9) or fully human monoclonal antibody (D4). During the treatment, the growth of tumors was monitored once weekly with a calliper.

Figure 6:
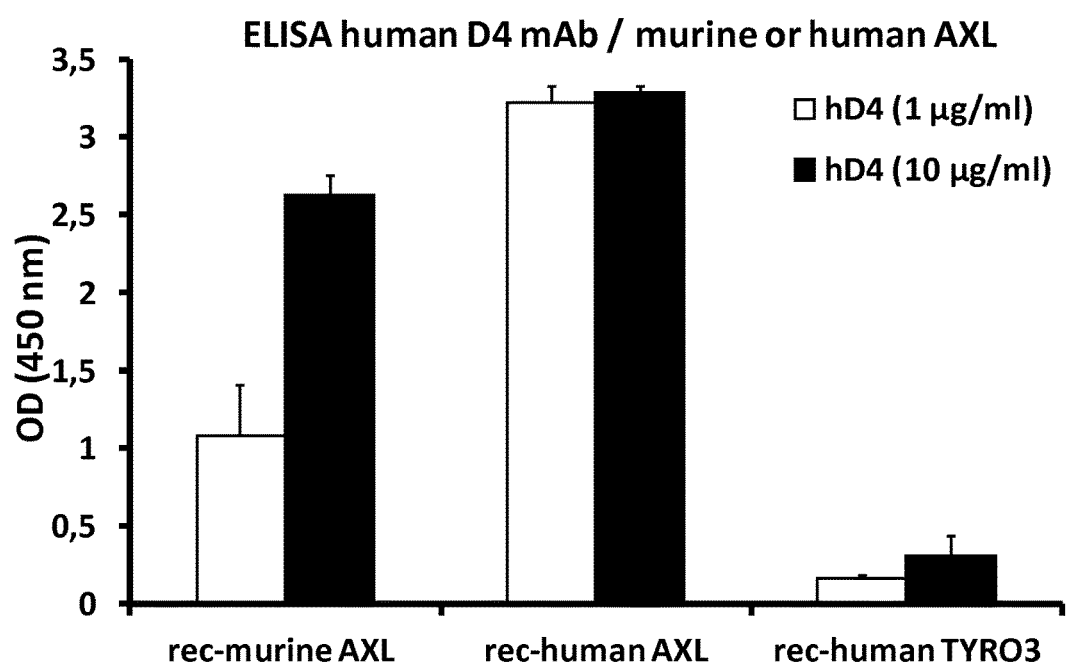

FIG. 6: shows that the human monoclonal antibody D4 is able to cross react between the murine and human form of AXL.

EXAMPLES

Example 1

Figure 1:
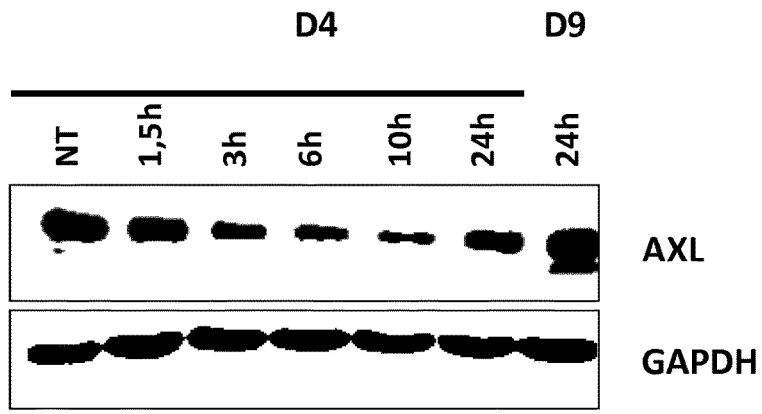
FIG. 1 shows that the human monoclonal antibody D4 induces degradation of the AXL receptor more efficiently than the antibody D9 disclosed in WO 2012175691.
Figure 2:
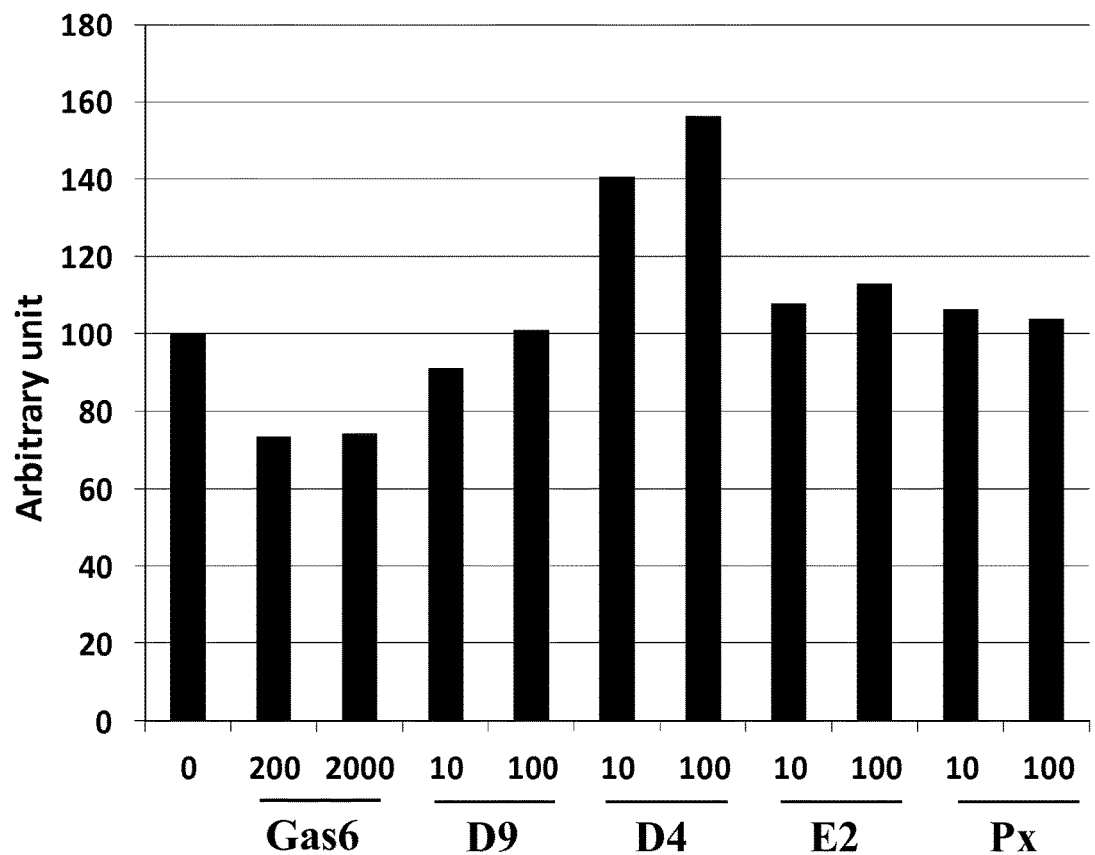
FIG. 2 shows that the human monoclonal antibody scFv-Fc D4 induces homodimerization of the AXL receptor more efficiently than the antibody D9 disclosed in WO 2012175691.
Figure 3:
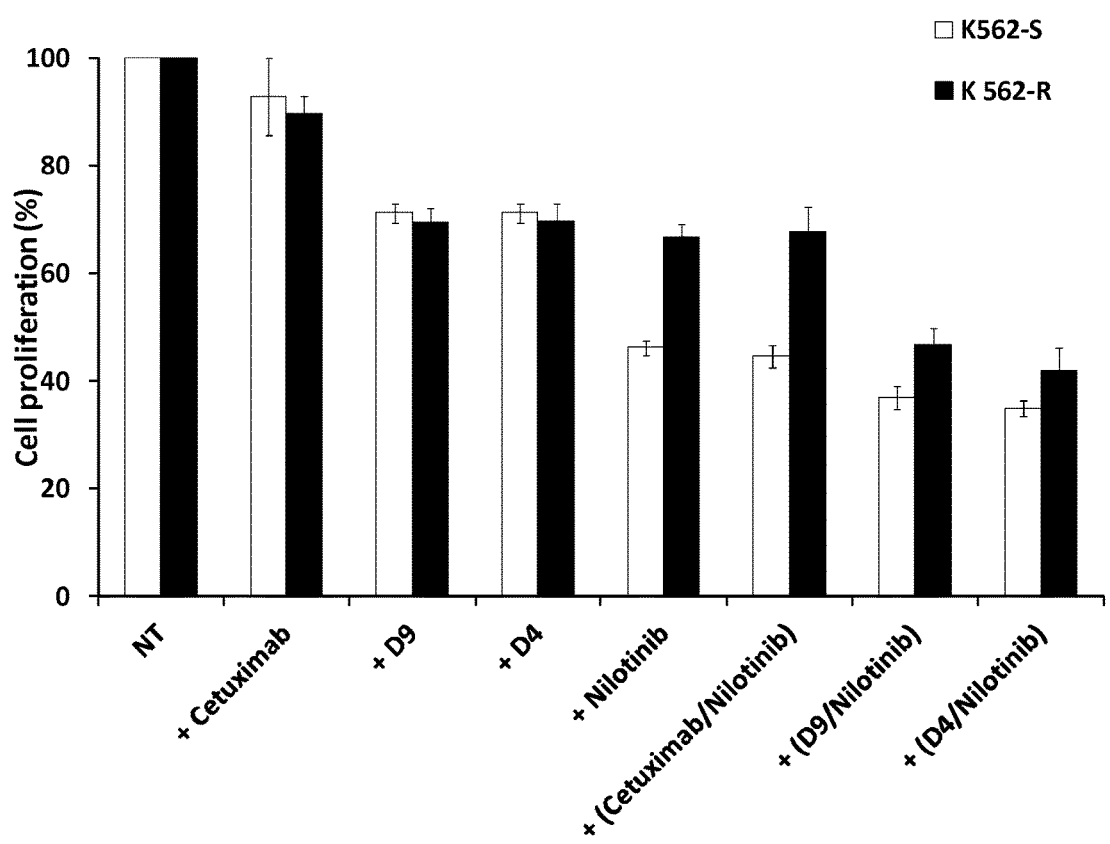
FIG. 3 shows the proliferation of K562-S and K562-R CML cell lines, following a treatment of 3 days with the Cetuximab antibody (negative control), the murine monoclonal antibody D9 and the human monoclonal antibody D4 alone or in combination with Nilotinib.
Figure 4:
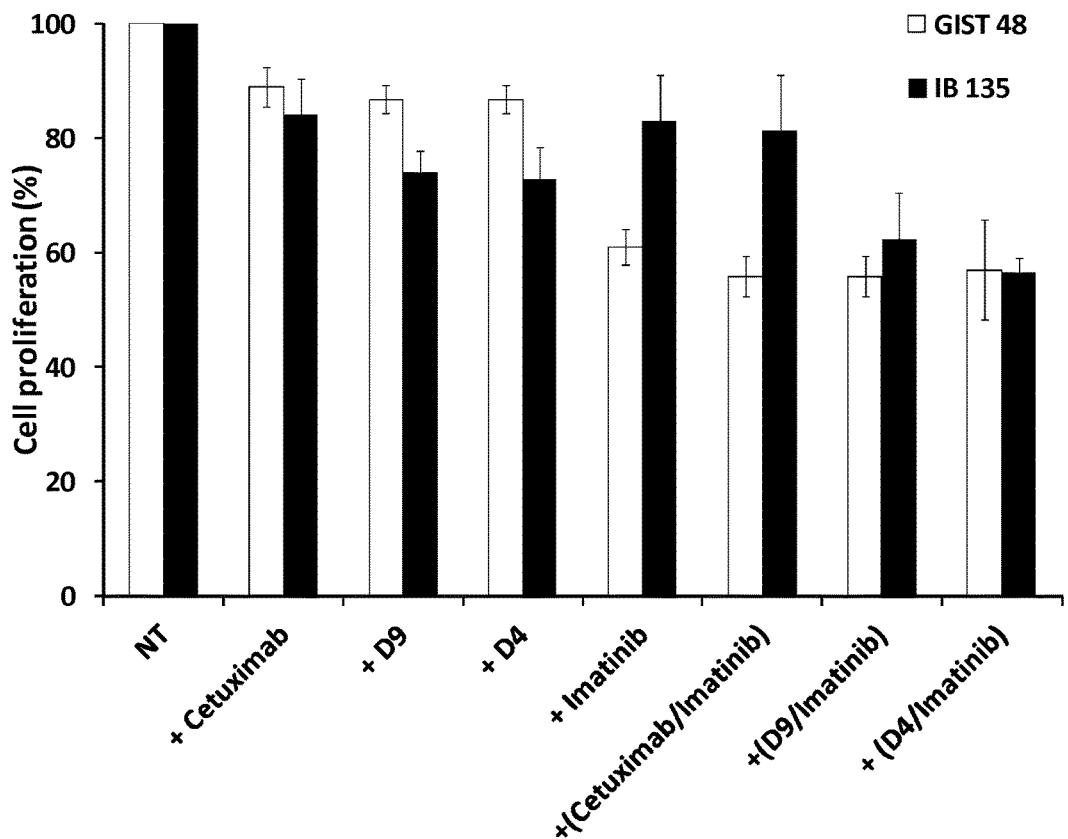
FIG. 4 shows the proliferation of GIST48 and IB135 GIST cell lines, following a treatment of 3 days with the Cetuximab antibody (negative control), the murine monoclonal antibody D9 and the human monoclonal antibody D4 alone or in combination with Imatinib.

The inventors have generated in the laboratory full human mAbs specific to the extracellular domain of AXL receptor and screened one (i.e. the D4 human monoclonal antibody) able to induce internalization and degradation of AXL receptor on cell surface membrane (FIG. 1) and to cross react between the murine and human form of AXL (FIG. 6). The antibody is able to induce homodimerization of the receptor (FIG. 2). Consequently, tumor cells treated with this mAb showed a dramatic decrease of the presence of AXL receptor at their cell surface and treated cells are no more able to respond to GAS6, the natural ligand of AXL. This also resulted in an inhibition of AXL phosphorylation, as well as a strong inhibition of cell proliferation in vitro. We have demonstrated that treatment with our anti-AXL mAb restores the sensibility to Nilotinib of resistant AXL-overexpressing CML cells (FIG. 3). Moreover, the same effect has been observed on treated Imatinib-resistant GIST cells (FIG. 4).

Example 2

The Human Monoclonal Antibody of the Invention Reduces Pancreatic Cancer Growth In Vivo All in vivo experiments were performed in compliance with the French guidelines for experimental animal studies (Agreement no. C34-172-27). Six-week old female athymic nude mice were purchased from Harlan. Pancreatic carcinoma cells ($3.5 \times 10^6$, BXPC3) were implanted into right flank of athymic nude mice. Tumor-bearing mice were randomized in different treatment groups when tumors reached an approximate volume of 100 mm3. The mice were treated by intraperitoneal injections with vehicle (0.9% NaCl); a mouse anti-AXL monoclonal antibody 20G7-D9 (D9), or the human monoclonal antibody D4 alone at 300 µg/injection (twice a week for 4 consecutive weeks). Tumor volume was measured weekly with a caliper. The anti-AXL antibodies and in particular the human antibody D4 decrease tumor growth of pancreatic xenografts (FIG. 5).

REFERENCES

Throughout this application, various references describe the state of the art to which this invention pertains. The disclosures of these references are hereby incorporated by reference into the present disclosure.

The invention claimed is:

1. A human monoclonal antibody, or an antigen-binding fragment thereof, against AXL, comprising
a heavy chain variable region (VH) comprising a H-CDR1 of D4, a H-CDR2 of D4 and a H-CDR3 of D4; and
a light chain variable region (VL) comprising a L-CDR1 of D4, a L-CDR2 of D4 and a L-CDR3 of D4;
wherein
the H-CDR1 of D4 is defined by the sequence ranging from the amino acid residue at position 31 to the amino acid residue at position 35 in SEQ ID NO:1,
the H-CDR2 of D4 is defined by the sequence ranging from the amino acid residue at position 50 to the amino acid residue at position 66 in SEQ ID NO:1,
the H-CDR3 of D4 is defined by the sequence ranging from the amino acid residue at position 99 to the amino acid residue at position 108 in SEQ ID NO:1,
the L-CDR1 of D4 is defined by the sequence ranging from the amino acid residue at position 23 to the amino acid residue at position 36 in SEQ ID NO:2,
the L-CDR2 of D4 is defined by the sequence ranging from the amino acid residue at position 52 to the amino acid residue at position 58 in SEQ ID NO:2, and,
the L-CDR3 of D4 is defined by the sequence ranging from the amino acid residue at position 91 to the amino acid residue at position 100 in SEQ ID NO:2.

2. The human monoclonal antibody of claim 1, wherein the VH has an amino acid sequence identity as set forth in SEQ ID NO:1.

3. The human monoclonal antibody of claim 1, wherein the VL has an amino acid sequence identity as set forth in SEQ ID NO:2.

4. The human monoclonal antibody of claim 1 which is an antibody comprising the VH having an amino acid sequence identity as set forth in SEQ ID NO:1 and the VL having a sequence identity as set forth in SEQ ID NO:2.

5. The antigen-binding fragment of the human monoclonal antibody of claim 1 which is selected from the group consisting of Fv, Fab, F(ab')2, Fab', dsFv, scFv, sc(Fv)2 and diabodies.

6. The human monoclonal antibody of claim 1 which is conjugated to a therapeutic moiety selected from the group consisting of a cytotoxin, a chemotherapeutic agent, a cytokine, an immunosuppressant, an immune stimulator, a lytic peptide, and a radioisotope.

7. The human monoclonal of claim 6 which is conjugated to auristatin.

8. A pharmaceutical composition which comprises the human monoclonal antibody of claim 1 and a pharmaceutically acceptable carrier.

9. A method of treating cancer in a subject in need thereof comprising administering to the subject a therapeutically effective amount of the human monoclonal antibody of claim 1.

10. A human monoclonal antibody against AXL, comprising
a heavy chain variable region (VH) having the H-CDR1 of D4, the H-CDR2 of D4 and the H-CDR3 of D4; and
a light chain variable region (VL) having the L-CDR1 of D4, the L-CDR2 of D4 and the L-CDR3 of D4.

11. A human monoclonal antibody against AXL, comprising a heavy chain variable region (VH) having an amino acid sequence as set forth in SEQ ID NO:1 and a light chain variable region (VL) having an amino acid sequence as set forth in identical to SEQ ID NO:2.

12. A nucleic acid molecule which encodes the VH and the VL of the human monoclonal antibody or the antigen-binding fragment thereof of claim 1.

13. A vector comprising the nucleicacid molecule of claim 12.

14. A host cell comprising the nucleicacid of claim 12.

* * * * *